United States Patent [19]
Grahek et al.

[11] Patent Number: 5,854,390
[45] Date of Patent: Dec. 29, 1998

[54] CHROMATOGRAPHIC PURIFICATION OF VANCOMYCIN HYDROCHLORIDE BY USE OF PREPARATIVE HPLC

[75] Inventors: Rok Grahek, Kranj; Andrej Bastarda, Ljubljana, both of Slovenia

[73] Assignee: LEK, tovarna farmacevtskih in kemicnih izdelkov, d.d., Ljubljana, Slovenia

[21] Appl. No.: 875,442

[22] PCT Filed: Feb. 6, 1996

[86] PCT No.: PCT/SI96/00002

§ 371 Date: Jul. 28, 1997

§ 102(e) Date: Jul. 28, 1997

[87] PCT Pub. No.: WO96/24614

PCT Pub. Date: Aug. 15, 1996

[30] Foreign Application Priority Data

Feb. 7, 1995 [SI] Slovenia ............... P-9500040

[51] Int. Cl.⁶ .................. C07K 5/12; A61K 38/12
[52] U.S. Cl. ........................ 530/344; 424/124
[58] Field of Search ............... 530/344; 424/124

[56] References Cited

U.S. PATENT DOCUMENTS 5,043,423  8/1991  Viscomi et al. ............... 530/344

OTHER PUBLICATIONS

Subramanian, G. et al.: Displacement Chromatography of Biomolecules. J. of Chromatography vol. 439, pp. 341–351, 1988.

*Primary Examiner*—Alan L. Rotman
*Assistant Examiner*—Charanjit S. Aulakh
*Attorney, Agent, or Firm*—Pollock, Vande Sande and Amernick

[57] ABSTRACT

The present invention discloses a new method for the purification of vancomycin hydrochloride by preparative HPLC (method of displacement chromatography), whereby the chromatographic purity of the product is essentialy improved.

The chromatography is performed on a reverse stationary phase with a mobile phase consisting of an organic or inorganic acid or of a buffer with possible additives, with different displacing agents, at a defined pH and temperature as well as the amount and concentration of vancomycin hydrochloride.

The process is distinguished by the excellent yield and exceptional chromatographic purity 95.5% area of the obtained product and, besides, it represents an ecologically irreproachable process.

The vancomycin hydrochloride purified according to the present invention is useful for all types of application since the portion of impurities it contains is for one third lower than in hitherto known commercially available products.

34 Claims, No Drawings

CHROMATOGRAPHIC PURIFICATION OF VANCOMYCIN HYDROCHLORIDE BY USE OF PREPARATIVE HPLC

TECHNICAL FIELD

International Patent Classification: C 07 K 9/10; C 07 K 3/20

This application is a 371 of PCT/SI96/00002, which is now published as WO96/24614 on Aug. 15, 1995.

The present invention relates to a new process for the purification of crude vancomycin hydrochloride by the use of preparative HPLC (a method of reverse phase displacement chromatography), whereby the chromatographic purity of the product is improved.

Vancomycin is a tricyclic amphoteric glycopeptide antibiotic in a salt (hydrochloride) form having the empirical formula $C_{66}H_{75}Cl_2N_9O_{24}$.HCl and the molecular weight of 1.486 g/mol. The preparation of vancomycin by the fermentation of microorganisms Amycolatopsis orientalis (previously Nocardia onentalis) is described in more detail in U.S. Pat. No. 3,067,099. Lyophilized vancomycin hydrochloride has an off-white colour and with water it forms a clear solution having a pH between 2.5 and 4.5.

Vancomycin hydrochloride is particularly used for the initial treatment of serious or severe infections caused by Gram-negative staphylococci resistant against β-lactam antibiotics as well as in patients who are penicillin-sensitive or do not respond to penicillins and cephalosporines.

Vancomycin hydrochloride is commercially available in oral (solution and capsules/pulvules) and parenteral (sterile intravenous solution in vials) forms.

Oral use of vancomycin hydrochloride is only allowed in treating staphylococcal enterocolitis where the parenteral form is not effective. For all other types of indications only parenteral use is relevant.

Vancomycin hydrochloride alone or in combination with other aminoglycosides is also useful in treating staphylococcal, streptococcal, enterococcal or diphtherial endocarditis.

To reduce the possibility of side effects a high chromatographic purity of antibiotics is very important in some kinds of their usage, which cannot be achieved by hitherto existing purification processes.

However, it has been achieved by the new process according to the present invention, which is more acceptable also from the ecological point of view due to the use of non-toxic solvents.

TECHNICAL PROBLEM

In the preparation of vancomycin consisting of a multi-stage process involving fermentation, isolation and various means of purification, sometimes a product with a more distinctive colour and with an unpleasant odour is obtained and also the yield and purity are reduced.

Since vancomycin represents a very interesting and valuable product, a constant need for new processes for effective isolation thereof exists. By the use of the most hitherto known processes and also by a multiple repetition of the processes, the portion of several kinds of impurities cannot be reduced so as to obtain vancomycin with an improved purity grade.

Therefore the aim of present invention is to prepare vancomycin hydrochloride of a new quality class having a considerably greater chromatographic purity than any commercialy available products, which is shown by its whiter colour, and also to obtain a high yield by using an ecologically irreproachable process.

PRIOR ART

From patent and other literature a number of methods for the preparation of glycopeptide antibiotics from the fermentation medium as well as for the purification of the fermentation products are known, which include precipitation processes using NaOH (EP 323,150, U.S. Pat. No. 5,037,652, JP 5,244,964) or ethanol (U.S. Pat. No. 4,868,285), formation of phosphates (EP 145,484) or complexes with peptides (U.S. Pat. No. 4,667,024) or imidazole (U.S. Pat. No. 4,868,285), processes for adsorption onto different polymer resins (U.S. Pat. No. 4,440,753, U.S. Pat. No. 4,845,194, U.S. Pat. No. 4,874,843, U.S. Pat. No. 5,149,784, WO 91/08,300, U.S. Pat. No. 5,258,495 or WO 93/21,207) as well as salting out and precipitation (U.S. Pat. No. 5,235,037).

In these patents chromatography is only used for preparative purposes in U.S. Pat. No. 4,667,024 (affinity) and in a part of the process in WO 91/08,300 (ion exchange).

Reverse phase displacement chromatography essentially differs from both types of chromatographies used so far.

The method of displacement chromatography has been known since 1943 and is based on the principle that in a sample the balance between stationary phase (SP) and mobile phase (MP) is shifted the direction of SP. Single components of the sample displace each other like a train and the displacing agent with the greater affinity to SP pushes this train by fractions out of the column. At purification the substance is also concentrated. However, due to the lack of effective columns and the complexity of nonlinear chromatography this method was only put into practice in 1981: Cs. Horvath et al., J. Chromatogr., 215 (1981) 295; J. Chromatogr., 330 (1985) 1; J. Chromatogr., 440 (1988) 157. In these articles analytical and preparative separation and purification of biologically active peptides and polymyxin antibiotics (polypeptide) by reverse phase chromatography by means of displacement are described. For polymyxins there were used octadecyl silica gel columns (250×4.6 mm) with the particle size of 5 μm, 10% acetonitrile in water as the mobile phase and various tetraalkyl ammonium halides as displacing agents.

Similar columns were used also later in the investigations in the field of displacement chromatography: S. M. Cramer et al., Enzyme Microb. Technol., 11 (1989) 74; Prep. Chromatogr., 1 (1988) 29; J. Chromatogr., 394 (1987) 305; J. Chromatogr., 439 (1988) 341; J. Chromatogr., 454 (1988) 1 (theoretical optimization); A. Felinger et al., J. Chromatogr., 609 (1992) 35 (theoretical optimization); the mobile phase was methanol in a phosphate buffer and the displacing agent was 2-(2-t-butoxyetoxy)-ethanol (BEE) in acetonitrile and Na-acetate. As samples the different peptides, proteins and antibiotic cephalosporin C were used.

U.S. Pat. No. 5,043,423 (27.08.1991) or EP 416,416 disclose a method for purification of some particular low-molecular (below 1000 Daltons) peptides (particularly tuftsin and its synthetic derivatives) by ion exchange displacement chromatography, wherein the SP is a cation exchange resin, the transport solvent is water or various diluted strong acids and a displacing agent (triethylene tetraammonium salt) in different concentrations is used.

Commercially available lyophilized vancomycin hydrochloride is in the form of an off-white powder.

TECHNICAL SOLUTION

The manufacturers of the antibiotics are constantly faced with the need to ensure a high yield of medicinal substances with a high chromatographic purity, at as low production costs as possible and, possibly, at a favourable ecological balance. This problem is particularly evident at the preparation of vancomycin due to the considerable portion of impurities in the crude product, which results in high costs for its purification. Besides, vancomycin is more polar than peptides due to sugar moieties present in its molecule.

Therefore the present process for the purification of vancomycin hydrochloride by displacement chromatography represents an essential improvement over the prior art since the portion of impurities in the obtained substance is at least for one third lower than in the purest hitherto known, commercially available sample, which is evident from the very white colour of the product.

The object of the present invention is a process for the purification of vancomycin hydrochloride by reverse phase displacement chromatography including the following stages:

1. conditioning the column with the selected mobile phase,
2. applying vancomycin hydrochloride dissolved in the mobile phase,
3. applying a displacing agent to displace vancomycin hydrochloride out of the column and collecting the fractions,
4. analyzing the fractions by analytical HPLC and combining the fractions according to their quality,
5. lyophilization,
6. regeneration—washing the column with a mixture of alcohol-water to eluate the displacing agent.

This method is useful for the purification of different peptide substances, particularly more polar glycopeptides having a molecular weight about 5.000 g/mol.

The stationary phase is a reverse phase, which may be natural (silica gel with alkyl chains of different lengths) or a synthetic crosslinked polymer (consisting of styrene and divinylbenzene). The particle size of the stationary phase is within the range from a few $\mu$m to several 100 $\mu$m.

The pH of the mobile phase must be moderately acidic because of a lower stability of vancomycin hydrochloride in an alkaline medium and is adjusted by the concentration of the acid or by the formation of an appropriate buffer. The mobile phase is a diluted organic acid, a halogenated organic or inorganic acid such as formic acid, acetic acid, propionic acid, hydrochloric acid, boric acid, phosphoric acid and sulfuric acid or buffers thereof formed with alkali metal cations, ammonia or amines. To achieve a better wetting of the stationary phase, an amount of a few % of an alcohol, acetonitrile, tetrahydrofuran or of a combination thereof can be added to the mobile phase. After the completed chromatography the stationary phase is regenerated with 20–100% of a lower alcohol in a water solution.

The displacing agent can be:

an alcohol with at least a $C_4$-chain (better results are achieved with n-alcohols), a (di)oxyalcohol (alcohol-ether)—a compound of the type R-O-Y-OH or R-O-Y-O-Y-OH with an ether bond and a hydroxyl end, wherein R is an alkyl radical and Y is an alkylene group, a quaternary ammonium salt with a general formula $R_1R_2R_3R_4NX$, wherein $R_1$, $R_2$, $R_3$ and $R_4$ being the same or different represent phenyl, benzyl or a $C_1$–$C_{12}$-alkyl radical, X is chloride, bromide or iodide, sodium dodecyl sulfate or a hydroxy derivative thereof.

Since it is possible to replace the toxic methanol in the mobile phase with the less toxic ethanol without any real difficulties, the present invention represents a considerable improvement over the prior art also from the ecological point of view due to a simpler removal of the waste solvents.

The present invention is illustrated but in no way limited by the following example.

EXAMPLE

Experimental data for displacement chromatography are as follows:

The stationary phase was an octadecyl silica gel column 50×200 mm (reverse phase) with a particle size of 12 $\mu$m and the mass of the stationary phase was 200 g.

The mobile phase (312 ml) with a flow rate of 45 ml/min consisted of 3% methanol or ethanol in acetic acid having a concentration of 40 mmol/l so that the pH was 3.0. The mobile phase was displaced by n-pentanol with the concentration of 200 mmol/l of mobile phase. The entering crude vancomycin hydrochloride (25 g) had a concentration of 80 g/l of mobile phase. The deposit was 1 g of sample per 8 g of stationary phase or 64 mg of sample per 1 ml of stationary phase. The capacity of the process was 12.5 g of sample per hour.

The total yield of the obtained product was 90.6%. The product was separated into 3 fractions with the third fraction and, if necessary, the middle fraction being repeatedly purified.

| Fraction | Product portion | Chrom. purity | $T_{405}$ | Colour | Comparison with commercial sample |
|---|---|---|---|---|---|
| entering | — | 84.1% | 66% | yellow-brown | — |
| 95% | 57.8% | 95.5% | 88% | snow white | better |
| 92% | 20.8% | 92% | — | white | similar |
| recycled | 12.0% | 81% | — | yellowish | — |

$T_{405}$ is the permeability of a 5% solution.

We claim:

1. A method for the purification of vancomycin antibiotics by displacement chromatography characterized in that the stationary phase is a natural or synthetic reverse phase, the mobile phase is a diluted acid or buffer and the displacing agent is an alcohol an oxyalcohol (alcohol-ether), an alkali metal alkyl sulfate or derivative thereof or a tetraalkylammonium halide.

2. A method according to claim 1, characterized in that it is useful for the purification of vancomycin hydrochloride.

3. A method according to claim 1, characterized in that the stationary phase is octadecyl silica gel.

4. A method according to claim 1, characterized in that the stationary phase is selected from synthetic polymers consisting of styrene and divinylbenzene.

5. A method according to claim 1, characterized in that the mean diameter of the particles constituting the stationary phase is between about 2 and about 100 $\mu$m.

6. A method according to claim 1, characterized in that the mean diameter of the particles constituting the stationary phase is about 12 $\mu$m.

7. A method according to claim 1, characterized in that the ratio between the amount of the applied substance and the stationary phase is about 1:3 at the most.

8. A method according to claim 7, characterized in that the ratio between the amount of the applied substance and the stationary phase is about 1:8.

9. A method according, to claim 1, characterized in that the concentration of the substance in the mobile phase is between about 0.5 mmol/l and about 150 mmol/l.

10. A method according to claim 9, characterized in that the concentration of the substance in the mobile phase is about 50 mmol/l.

11. A method according to claim 1, characterized in that the pH of the mobile phase is between about 2 and about 10.

12. A method according to claim 11, characterized in that the pH of the mobile phase is between about 2 and about 6.

13. A method according to claim 11, characterized in that the acid in the mobile phase is an organic acid, namely formic acid, acetic acid or propionic acid, halogenated derivative thereof or an organic or inorganic buffer of one of these acids.

14. A method according to claim 13, characterized in that the acid in the mobile phase is acetic acid or ammonium acetate buffer.

15. A method according to claim 11, characterized in that the acid in the mobile phase is an inorganic one, namely HCl, or in the form of a borate, phosphate, sulfate or chloride buffer, the cations being inorganic cations, ammonia or different amines.

16. A method according to claim 11, characterized in that the concentration of the acid in the mobile phase is between about 2 and about 500 mmol/l.

17. A method according to claim 16, characterized in that the concentration of the acid in the mobile phase is about 40 mmol/l.

18. A method according to claim 1, characterized in that to the mobile phase methanol, ethanol, propanol, acetonitrile, tetrahydrofuran or a combination thereof is added.

19. A method according to claim 18, characterize in that the alcohol in the mobile phase is methanol.

20. A method according to claim 18, characterize in that the alcohol in the mobile phase is ethanol.

21. A method according to claim 18, characterized, in that the concentration of the additive to the mobile phase is between about 0.5 and about 10%.

22. A method according to claim 21, characterized in that the concentration of the additive to the mobile phase is about 2%.

23. A method according to claim 1, characterized in that the displacing agent is an alcohol having at least a $C_4$-chain.

24. A method accord to claim 23, characterized in that the displacing agent is butanol.

25. A method according to claim 23, characterized in that the displacing agent is pentanol.

26. A method according to claim 1, characterized in that the displacing agent is 2-etoyethanol.

27. A method according to claim 1, characterized in that the displacing agent is tetraalkyl ammonium halide.

28. A method according to claim 27, characterized in that the displacing agent is cetyl trimethyl ammonium bromide.

29. A method according to claim 1, characterized in that the displacing agent is an alkali metal alkyl sulfate or its derivative having an —OH group at the alkyl chain.

30. A method according to claim 29, characterized in that the displacing agent is sodium dodecyl sulfate.

31. A method according to claim 1, characterized in that the concentration of the displacing agent in the mobile phase is between about 10 and about 1000 mmol/l.

32. A method according to claim 31, characterized in that the concentration of the displacing agent in the mobile phase is about 200 mmol/l.

33. A method according to claim 1 wherein said displacing agent is an alcohol.

34. A method according to claim 1 wherein said displacing agent is a monoalcohol or an alcohol diether.

* * * * *